United States Patent [19]

Stengelin et al.

[11] Patent Number: 5,227,293

[45] Date of Patent: Jul. 13, 1993

[54] FUSION PROTEINS, THEIR PREPARATION AND USE

[75] Inventors: Siegfried Stengelin, Hofheim am Taunus; Wolfgang Ulmer; Paul Habermann, both of Eppstein/Taunus; Eugen Uhlmann, Glashutten/Taunus, all of Fed. Rep. of Germany; Brian Seed, Boston, Mass.

[73] Assignees: The General Hospital Corporation, Boston, Mass.; Hoechst Aktiengesellschaft, Frankfurt, Fed. Rep. of Germany

[21] Appl. No.: 838,221

[22] Filed: Apr. 23, 1992

Related U.S. Application Data

[63] Continuation-in-part of Ser. No. 399,874, Aug. 29, 1989, abandoned.

[51] Int. Cl.[5] .................... C12N 15/12; C12N 15/62
[52] U.S. Cl. .................... 435/69.7; 435/69.1; 435/172.3
[58] Field of Search .................... 435/69.1, 69.7, 172.3

[56] References Cited

U.S. PATENT DOCUMENTS

| | | | | |
|---|---|---|---|---|
| 4,366,246 | 12/1982 | Riggs | | 435/68 |
| 4,431,739 | 2/1984 | Riggs | | 435/253 |
| 4,652,639 | 3/1987 | Stabinsky | | 536/27 |
| 4,769,326 | 9/1988 | Rutter | | 435/68 |

FOREIGN PATENT DOCUMENTS

| | | |
|---|---|---|
| 60565/86 | 1/1987 | Australia . |
| 15631/88 | 11/1988 | Australia . |
| 16379/88 | 11/1988 | Australia . |
| 36718/89 | 1/1990 | Australia . |
| 0211299 | 2/1987 | European Pat. Off. . |
| 0290005 | 11/1988 | European Pat. Off. . |
| 0292763 | 11/1988 | European Pat. Off. . |
| 0292803 | 11/1988 | European Pat. Off. . |
| 0347781 | 12/1989 | European Pat. Off. . |

OTHER PUBLICATIONS

Oliphant, A. R. et al., *Gene*, 44:177–183 (1986).
Butt, T. R., et al., *Proc. Natl. Acad. Sci. USA*, 86:2540–2544 (1989).
Bachmair, A. et al., *Science*, 234:179–186 (1986).
Reidharr-Olson, J. F. et al., *Science*, 241:53–57 (1988).
Saiki, R. K. et al., *Science*, 239:487–491 (1988).
Aota, S. et al., *Nucl. Acids Res.*, 16 (suppl.):r315–r316, r391 and r402 only (1988).
Helfman, D. M. et al., *Proc. Natl. Acad. Sci. USA*, 80:31–35 (1983).
Ho, S. N. et al., *Gene*, 77:51–59 (1989).

*Primary Examiner*—Robert J. Hill, Jr.
*Assistant Examiner*—John D. Ulm
*Attorney, Agent, or Firm*—Sterne, Kessler, Goldstein & Fox

[57] ABSTRACT

Fusion proteins are obtained in high yields if a mixed oligonucleotide is constructed which codes for the ballast constituent of the fusion protein. The oligonucleotide mixture is introduced in a vector in such a manner that it is functionally linked to a regulatory region and to the structural gene for the desired protein. Appropriate host cells are transformed with the plasmid population obtained in this manner and the clones producing a high yield of coded fusion protein are selected.

17 Claims, 6 Drawing Sheets

FUSION PROTEINS, THEIR PREPARATION AND USE

This is a continuation-in-part of co-pending U.S. patent application Ser. No. 07/399,874 filed Aug. 29, 1989, abandoned.

FIELD OF THE INVENTION

The present invention relates to fusion proteins and a process for preparing fusion proteins. The invention also pertains to various oligonucleotide and amino acid sequences which make up fusion proteins of the present invention.

BACKGROUND OF THE INVENTION

Proteins, which in addition to the desired protein, also have an undesirable constituent or "ballast" constituent in the end product are referred to as fusion proteins. When proteins are prepared by genetic engineering, the intermediate stage of a fusion protein is utilized particularly if, in direct expression, the desired protein is decomposed relatively rapidly by host-endogenous proteases, causing reduced or entirely inadequate yields of the desired protein.

The magnitude of the ballast constituent of the fusion protein is usually selected in such a manner that an insoluble fusion protein is obtained. This insolubility not only provides the desired protection against the host-endogenous proteases but also permits easy separation from the soluble cell components. It is usually accepted that the proportion of the desired protein in the fusion protein is relatively small, i.e. that the cell produces a relatively large quantity of "ballast".

The preparation of fusion proteins with a short ballast constituent has been attempted. For example, a gene fusion was prepared which codes for a fusion protein from the first ten amino acids of β-galactosidase and somatostatin. However, it was observed that this short amino acid chain did not adequately protect the fusion protein against decomposition by the host-endogenous proteases (U.S. Pat. No. 4,366,246, Column 15, Paragraph 2).

From EP-A 0 290 005 and 0 292 763, we know of fusion proteins, the ballast constituent of which consists of a β-galactosidase fragment with more than 250 amino acids. These fusion proteins are insoluble, but they can easily be rendered soluble with urea (EP-A 0 290 005).

Although fusion proteins have been described in the art, the generation of fusion proteins with desirable traits such as protease resistance is a laborious procedure and often results in fusion proteins that have a number of undesirable characteristics. Thus, a need exists for an efficient process for producing fusion proteins with a number of attractive traits including protease resistance, proper folding, and effective cleavage of the ballast from the desired protein.

SUMMARY OF THE INVENTION

The present invention relates to a process for the preparation of fusion proteins. Fusion proteins of the present invention contain a desired protein and a ballast constituent. The process of the present invention involves generating an oligonucleotide library (mixture) coding for ballast constituents, inserting the mixed oligonucleotide (library) into a vector so that the oligonucleotide is functionally linked to a regulatory region and to the structural gene coding for the said desired protein, and transforming host cells with the so-obtained vector population. Transformants are then selected which express a fusion protein in high yield.

The process of the present invention further includes oligonucleotide coding for an amino acid or for a group of amino acids which allows an easy cleavage of the desired protein from the said ballast constituent. The cleavage may be enzymatic or chemical.

The invention also pertains to an oligonucleotide designed so that it leads to an insoluble fusion protein which can easily be solubilized. Fusion proteins of the present invention thus fulfill the requirements established for protease resistance.

Furthermore, oligonucleotide of the present invention may be designed so that the ballast constituent does not interfere with folding of the desired protein.

DETAILED DESCRIPTION OF THE INVENTION

Figure 1:
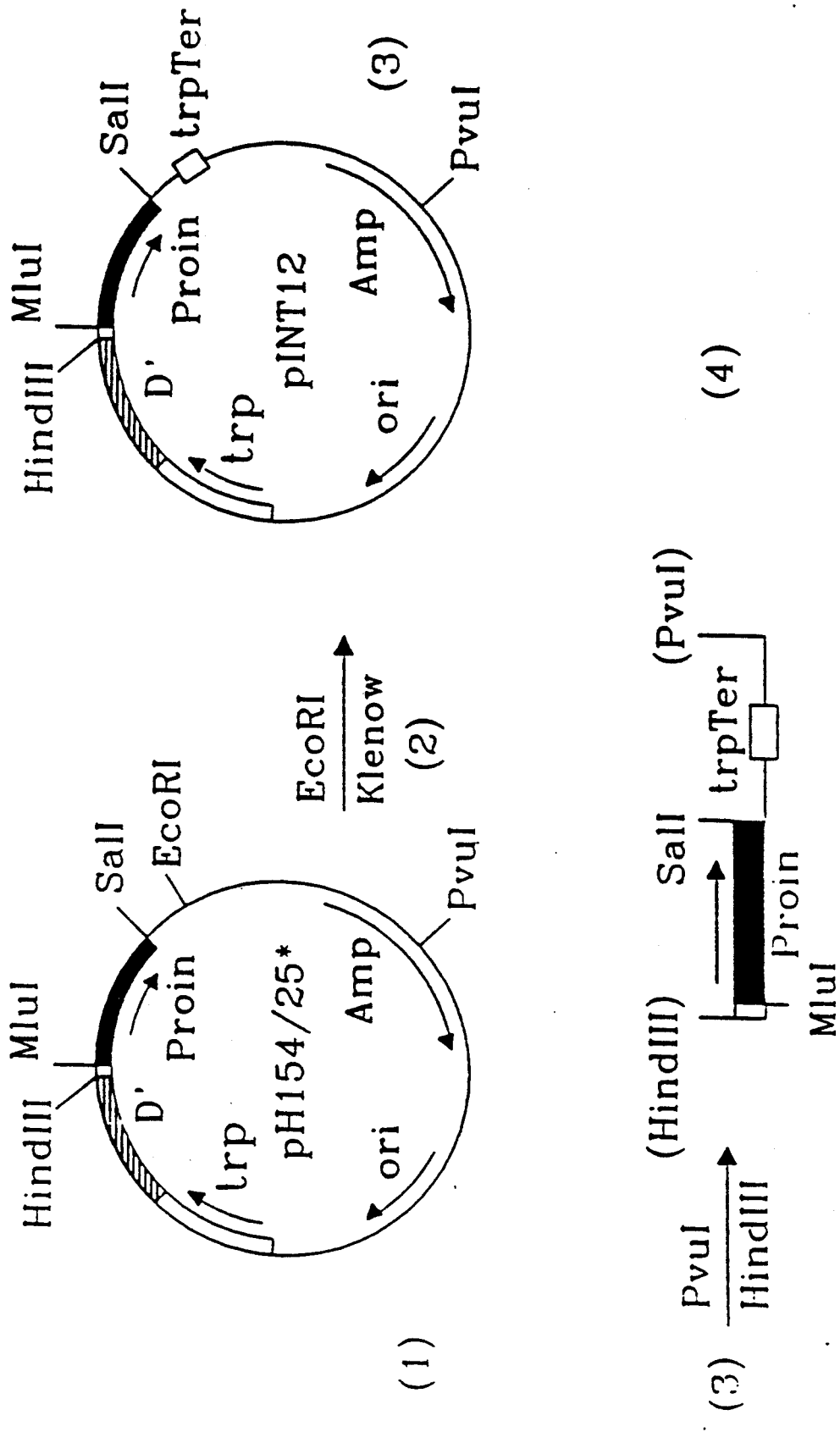
FIG. 1 and its continuation in FIG. 1a and FIG. 1b show the construction of plasmid population (gene bank) pINT4x from the known plasmid pH154/25* via plasmid pINT40. Other constructions have not been graphically presented because they are readily apparent from the figures.

The invention relates to a process for the preparation of a fusion protein characterized in that a mixed oligonucleotide is constructed which codes for the ballast constituent of the fusion protein. The oligonucleotide mixture is introduced in a vector in such a manner that it is functionally linked to a regulatory region and to the structural gene for the desired protein. Appropriate host cells are transformed with the plasmid population obtained in this manner, and the clones producing a high yield of coded fusion protein are selected. Advantageous embodiments of this invention are explained below:

The oligonucleotide advantageously codes at the 3'-end an amino acid or a group of amino acids which permits or permit easy and preferably enzymatic cleavage of the ballast constituent from the desired protein. According to another implementation form, an oligonucleotide is constructed that yields an insoluble fusion protein which can easily be made soluble. In particular, an oligonucleotide is preferably constructed which codes for a ballast constituent that does not disturb the folding of the desired protein.

For practical reasons, the construction, according to the invention, of the oligonucleotide for the ballast constituent causes the latter to be very short.

It was surprising to observe that, even when they have an extremely short ballast constituent, fusion proteins not only fulfill the requirements established for protease resistance, but are also produced at a high expression rate and, if desired, the fusion protein is insoluble, can easily be rendered soluble. In the dissolved or soluble state, the short ballast constituent according to the invention then permits a sterically favorable conformation of the desired protein so that it can be properly folded and easily separated from the ballast constituent.

If the desired protein is formed in a pro-form, the ballast constituent can be constituted in such a manner that its cleavage can occur concomitantly with the transformation of the pro-protein into the mature protein. In insulin preparation, for example, the ballast constituent and the C chain can be removed simultaneously, yielding a derivative of the mature insulin which can be transformed into insulin without any side reactions involving much loss.

The short ballast constituent according to the invention is actually shorter than the usual signal sequences of proteins and does not disturb the folding of the desired protein. It therefore need not be eliminated prior to the final processing step yielding the mature protein.

The oligonucleotide coding for the ballast constituent preferably contains the DNA sequence (coding strand)

$$(DCD)_x$$

in which D stands for A, G or T and x is 4–12, preferably 4–8.

In particular, the oligonucleotide is characterized by the DNA sequence (coding strand)

$$ATG\ (DCD)_y\ (NNN)_z$$

in which N in the NNN triplet stands for identical or different nucleotides, excluding stop codons, z is 1–4 and y+z is 6–12, preferably 6–10, wherein y is at least 4. It has proved advantageous for the oligonucleotide to have the DNA sequence (coding strand)

$$ATG\ (DCD)_{5-8}\ (NNN)$$

especially if it has the DNA sequence (coding strand)

$$ATG\ GCW\ (DCD)_{4-8}\ CGW$$

or, advantageously $$ATG\ GCA\ (DCD)_{4-7}\ CGW$$

in which W stands for A or T.

The above-mentioned DNA model sequences fulfill all of these requirements. Codon DCD codes for amino acids serine, threonine and alanine and therefore for a relatively hydrophilic protein chain. Stop codons are excluded and selection of the amino acids remains within manageable scope. The following is a particularly preferable embodiment of the DNA sequence for the ballast constituent, especially if the desired protein is proinsulin:

$$ATG\ GCW\ (DCD)_{y'}\ ACG\ CGW$$

or $$ATG\ GCD\ (DCD)_{y'}\ ACG\ CGT$$

in which y' signifies 3 to 6, especially 4 to 6.

The second codon, GCD, codes for alanine and completes the recognition sequence for the restriction enzyme NcoI, provided that the anterior regulation sequence ends with CC. The next to last triplet codes for threonine and, together with the codon CGT for arginine, represents the recognition sequence for restriction enzyme MluI. Consequently, this oligonucleotide can be easily and unambiguously incorporated in gene constructions.

The (NNN)z group codes in the 3' position for an amino acid or a group of amino acids that permits simple, and preferably enzymatic, separation of the ballast constituent from the subsequent protein desired. It is expedient to select the nucleotides in this group in such a manner that at the 3'-end they code the cleavage site of a restriction enzyme which permits linkage of the structural gene for the desired protein. It is also advantageous for the ATG start codon and if necessary the first DCD triplet to be incorporated into the recognition sequence of a restriction enzyme so that the gene for the ballast constituent according to the invention can easily be inserted in the usual vectors.

The upper limit of z is obtained on the one hand from the desired cleavage site for (enzymatic) cleavage of the fusion protein obtained, i.e. it encompasses codons, for example, for the amino acid sequence Ile-Glu-Gly-Arg, in case cleavage is to be carried out with factor Xa. In general, the upper limit for the sum of y and z is 12, since the ballast constituent should of course be as small as possible and, above all, not interfere with the folding of the desired protein.

For reasons of expediency, bacteria or low eukaryotic cells such as yeasts are preferred as the host organism in genetic engineering processes, provided that higher organisms are not required. In these processes, the expression of the heterologous gene is regulated by a homologous regulatory region, i.e. one that is intrinsic to the host or compatible with the host cell. If a prepeptide is expressed, it often occurs that the presequence is also heterologous to the host cell. In practice, this lacking "sequence harmony" frequently results in variable and unpredictable protein yields. Since the ballast sequence according to the invention is adapted to its environment, the selection process according to the invention yields a DNA construction characterized by this "sequence harmony".

The beginning and end of the ballast constituent are set in this construction: Methionine is at the beginning, and an amino acid or a group of amino acids that permit the desired separation of the ballast constituent from the desired protein is at the end. If, for example, the desired protein is proinsulin, as NNN a triplet coding for arginine is advantageously selected as the last codon as this permits the particularly favorable simultaneous cleaving off of the ballast constituent with the removal of the C chain. Of course, the end of the ballast constituent can also be an amino acid or a group of amino acids which allows a chemical cleavage, e.g. methionine, so that cleavage is possible with cyanogen bromide or chloride.

The intermediate amino acid sequence should be as short as possible so that folding of the desired protein is not affected. Moreover, this chain should be relatively hydrophilic so that solubilization is facilitated with undissolved fusion proteins and the fusion protein remains soluble. Cysteine residues are undesirable since they can interfere with the formation of the disulfide bridges.

The DNA coding for the ballast constituent is synthesized in the form of a mixed oligonucleotide; it is incorporated in a suitable expression plasmid immediately in front of the structural gene for the desired protein and E. coli is transformed with the gene bank obtained in this manner. Appropriate gene structures can be obtained in this way by the selection of bacterial clones that produce corresponding fusion proteins.

It was previously mentioned that the cleavage sites for the restriction enzymes at the beginning and end of the nucleotide sequence coding for the ballast constituent are to be regarded as examples only. Recognition sequences that encompass starting codon ATG and in which any nucleotides that follow may include the codon for suitable amino acids are, by way of example, also those for restriction enzymes AflIII, NdeI, NlaIII, NspHI or StyI. Since in the preferred embodiment arginine is to be at the end of the ballast sequence and since there are six different codons for arginine, additional appropriate restriction enzymes can also be found here for use instead of MluI, i.e., NruI, AvrII, AflIII, ClaI or HaeII.

However, it is also advantageous to use a "polymerase chain reaction" (PCR) according to Saiki, R.K. et al., Science 239:487–491, 1988, which can dispense with the construction of specific recognition sites for restriction enzymes.

It was previously indicated that limitation to the DNA sequence (DCD)x is for reasons of expediency and that this does not rule out other codons such as, for example, those for glycine, proline, lysine, methionine or asparagine.

The most efficient embodiment of this DNA sequence is obtained by selection of good producers of the fusion protein, i.e., the fusion protein containing proinsulin. This yields the most favorable combination of regulation sequence, ballast sequence and desired protein, as a result of which unfavorable combinations of promoter, ballast sequence and structural gene are avoided and good results are obtained with minimum expenditure in terms of the above-mentioned "sequence harmony".

Surprisingly, it was observed that the genes optimized for the ballast constituent according to the invention do not always contain the triplets preferred by $E.\ coli$. It was found that for Thr, codon ACA, which is used least frequently by $E.\ coli$, actually occurs frequently in the selected sequences. If, for example, the following amino acid sequence were optimized according to the preferred codon usage (p.c.u.) by $E.\ coli$ (p.c.u.: Aota, S. et al., Nucleic Acids Research 16 (supplement): r315, r316, r391, r402 (1988)), we would obtain a totally different gene structure than that obtained according to the invention (Cf.Table 1):

```
Ala  Thr  Thr  Ser  Thr  Ala  Thr  Thr
GCG  ACC  ACC  AGC  ACC  GCG  ACC  ACC  p.c.u.
GCA  ACA  ACA  TCA  ACA  GCA  ACT  ACG  invention
```

In the case of the fusion proteins with a proinsulin constituent, the initial starting point was a ballast constituent with 10 amino acids. The DNA sequence of the best producer then served as the base for variations in this sequence, whereupon it was noted that up to 3 amino acids can be eliminated without a noticeable loss in the relative expression rate. This finding is not only surprising, since it was unexpected that such a short ballast protein would be adequate, but also very advantageous since of course the relative proportion of proinsulin in the fusion protein increases as the ballast constituent decreases.

The significance of the ballast constituent in the protein is apparent from the following comparison: Human proinsulin contains 86 amino acids. If, for a fusion protein according to EP-A 0 290 005, we take the lower limit of 250 amino acids for the ballast constituent, the fusion protein has 336 amino acids, only about one quarter of which occur in the desired protein. By comparison, a fusion protein according to the invention with only 7 amino acids in the ballast constituent has 93 amino acids, the proinsulin constituent amounts to 92.5%. If the desired protein has many more amino acids than the proinsulin, the relationship between ballast and desired protein becomes even more favorable.

It has been mentioned on a number of occasions that as a desired protein proinsulin represents only one preferred embodiment of the invention. However, the invention also works with much larger fusion proteins for which a fusion protein with the active domain of human 3-hydroxy-3-methylglutaryl-coenzyme A-reductase (HMG) is mentioned as an example. This protein contains 461 amino acids. A gene coding for the latter is known e.g. from EP-A 292 803.

Having now generally described the invention, the same will be more readily understood through reference to the following examples which are provided by way of illustration, and are not intended to be limiting of the present invention, unless specified.

EXAMPLE 1

Construction of the gene bank and selection of a clone with high expression

If not otherwise indicated, all media are prepared according to Maniatis, T.; Fritsch, E. F. and Sambrook, J.: Molecular Cloning, Cold Spring Harbor Laboratory (1982). TP medium consists of M9CA medium but with a glucose and casamino acid content of 0.4% each. If not otherwise indicated, all media contain 50 μg/ml ampicillin. Bacterial growth during fermentation is determined by measurement of the optical density of the cultures at 600 nm (OD). Percentage data refer to weight if no other data is reported.

The starting material is plasmid pH154/25* (FIG. 1), which is known from EP-A 0 211 299 herein incorporated by reference. This plasmid contains a fusion protein gene (D'-Proin) linked to a trp-promoter and a resistance gene for resistance against the antibiotic ampicillin (Amp). The fusion protein gene codes a fusion protein that contains a fragment of the trpD-protein from $E.\ coli$ (D') and monkey proinsulin (Proin). The gene structure of the plasmid results in a polycistronic mRNA, which codes for both the fusion protein and the resistance gene product. To suppress the formation of excess resistance gene product, initially the (commercial) trp-transcription terminator sequence (trpTer) (2) is introduced between the two structural genes. To do so, the plasmid is opened with EcoRI and the protruding ends are filled in with Klenow polymerase. The resulting DNA fragment with blunt ends is linked with the terminator sequence (2)

```
5' AGCCCGCCTAATGAGCGGGCTTTTTTTT 3'           (2)
3' TCGGGCGGATTACTCGCCCGAAAAAAAA 5'
``` which results in plasmid pINT12 (FIG. 1-(3)).

Figure 1A:
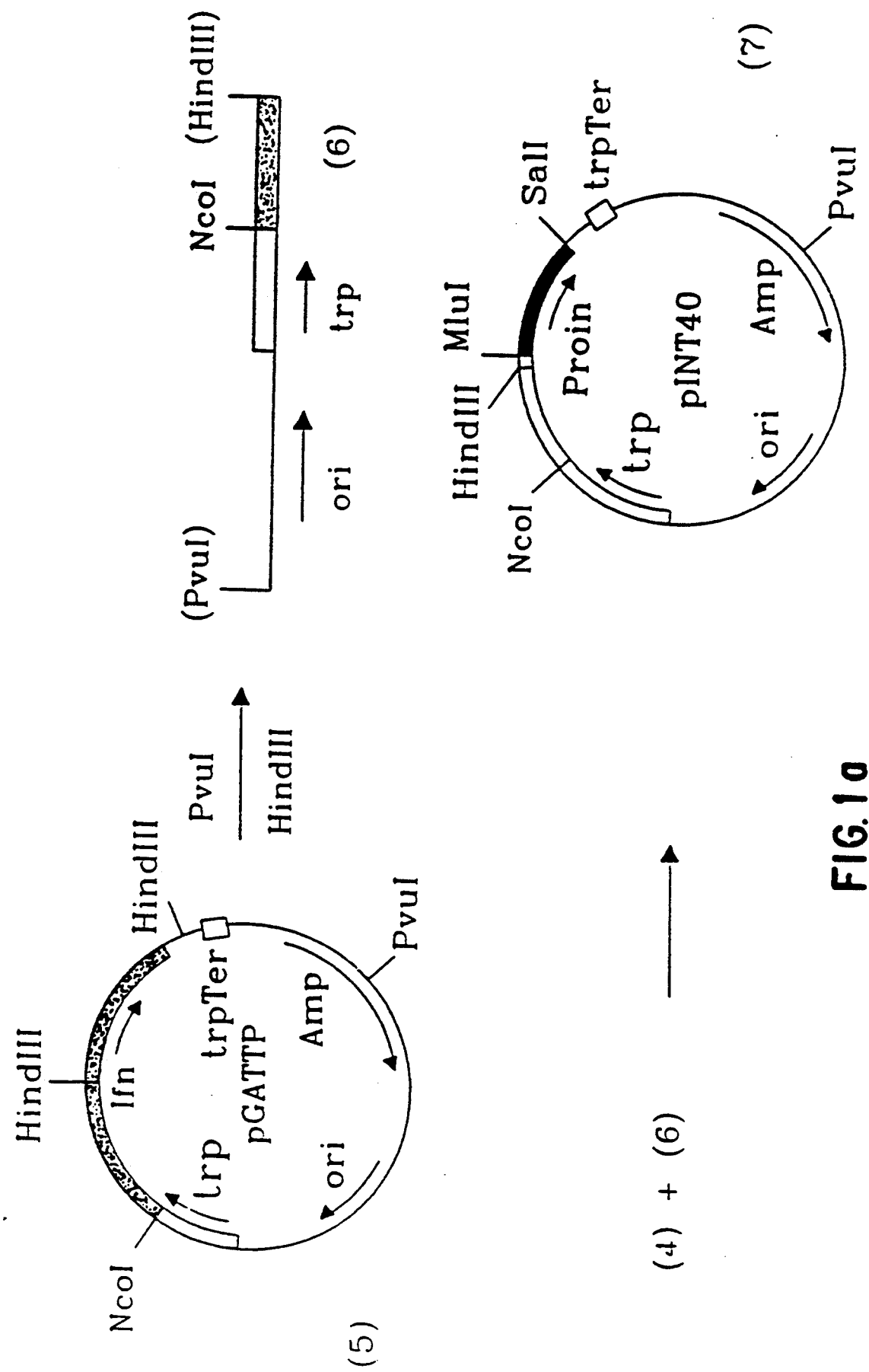
Figure 1B:
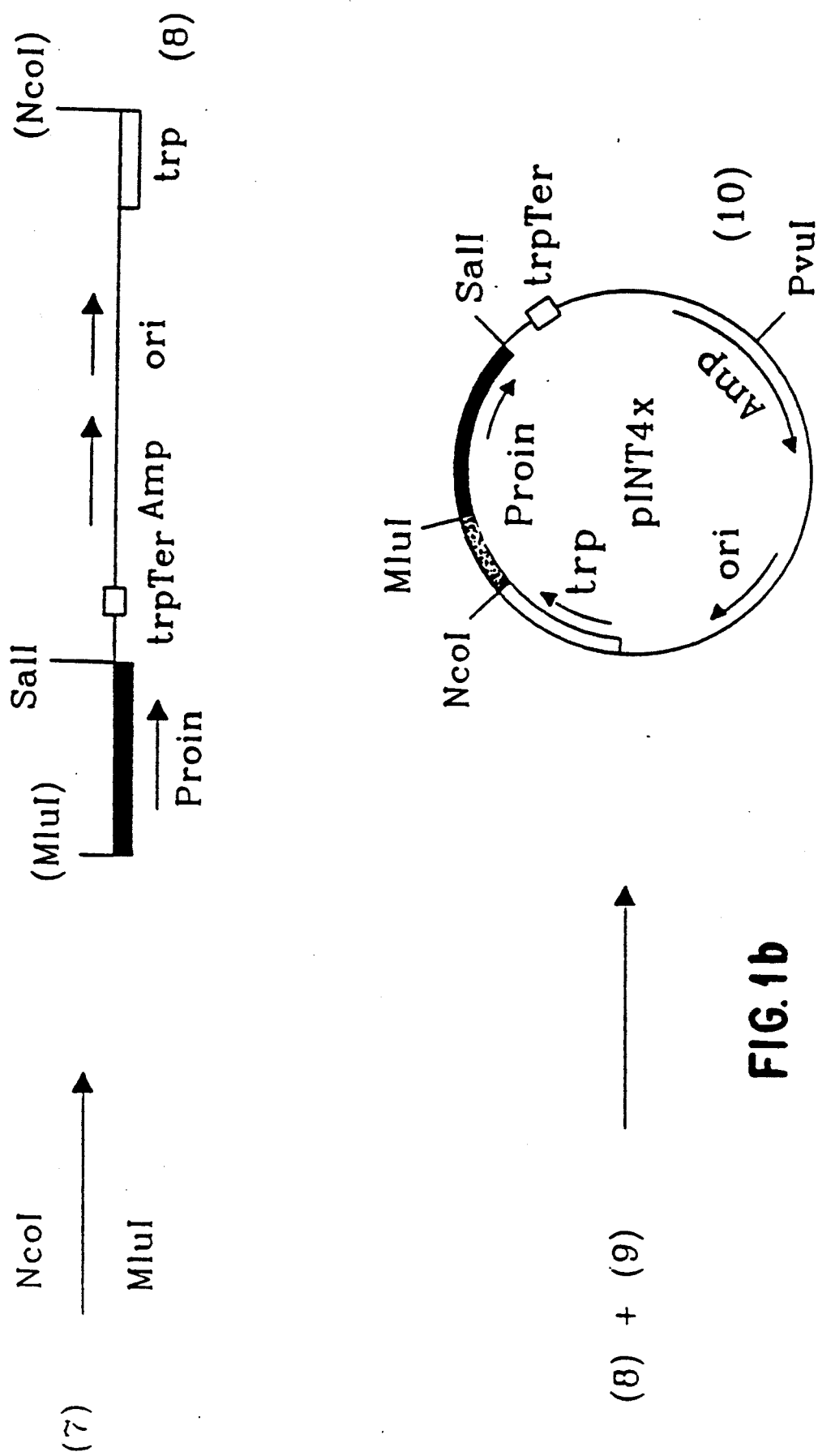

The starting plasmid pH154/25* contains a cleavage site for enzyme PvuI in the Amp gene, as well as a HindIII-cleavage site in the carboxyterminal area of the trpD-fragment. Both cleavage sites are therefore also contained in pINT12. By cutting the plasmid (FIG. 1-(3)) with PvuI and HindIII, it is split into two fragments from which the one containing the proinsulin gene (FIG. 1-(4)) is isolated. Plasmid pGATTP (FIG. 1a-(5)), which is structured in an analogous manner to (3) but which instead of the D'-Proin gene carries a gamma-interferon gene (Ifn) containing restriction cleavage sites NcoI and HindIII, is also cut with PvuI and HindIII and the fragment (FIG. 1a-(6)) with the promoter region is isolated. By ligation of this fragment (6) with the fragment (4) obtained from (3), we acquire plasmid pINT40 (FIG. 1a-(7)). The small fragment with the remainder of the gamma-interferon gene is cut from the latter with NcoI and MluI. The large fragment (FIG. 1b-(8)) is ligated with mixed olignonucleotide (9)

```
5' CATGGCDDCDDCDDCDDCDDCDDCDA3'         (9)
3'      CGHHGHHGHHGHHGHHGHHGHTGCGC5'
``` in which D stands for A, G or T and H signifies the complementary nucleotide. This results in plasmid population (gene bank) pINT4x (FIG. 1b-(10)). Mixed oligonucleotides of the present invention may be obtained by techniques well known to those of skill in the art.

The mixed oligonucleotide (9) is obtained from the synthetic mixed oligonucleotide (9a)

```
                                              (9a)
TTCGGGTACCGHHGHHGHHGHHGHHGHHGHTGCGCAG 5'
TTGCCCATGGC 3'
``` which is filled in with Klenow polymerase and cut with MluI and Nco.

The strain *E. coli* WS3110 is transformed with the plasmid population (10) and the bacteria are plated on LB agar dishes. Six of the resulting bacterial clones are tested for their ability to produce a fusion protein with an insulin constituent. For this purpose, overnight cultures of the clones are prepared in LB medium, and 100 μl aliquots of the cultures are mixed with 10.5 ml TP medium and shaken at 37° C. At OD600=1 the cultures are adjusted to 20 μg/ml 3-β-indolylacrylic acid (IAA), a solution of 40 mg glucose in 100 ml water is added and the preparation is shaken for another three hours at 37° C. Subsequently 6 OD equivalents of the culture are removed, the bacteria contained therein are harvested by centrifugation and resuspended in 300 μl test buffer (37.5 mM tris of pH 8.5, 7 M urea, 1% (w/v) SDS and 4% (v/v) 2-mercaptoethanol). The suspension is heated for five minutes, treated for two seconds with ultrasound to reduce viscosity and aliquots thereof are subsequently subjected to SDS-gel electrophoresis. With bacteria that produce fusion protein, we can expect a protein band with a molecular weight of 10,350 D. It is evident that one of the clones, pINT41 (Table 1), produces an appropriate protein in relatively large quantities while no such protein formation is seen with the remaining clones. An immune blot experiment with insulin-specific antibodies confirms that the protein coded by pINT41 contains an insulin constituent.

Table 1 shows the DNA and amino acid sequence of the ballast constituent for a number of plasmid constructs. In particular, table 1 illustrates the DNA and amino acid sequence of the ballast constituent in the pINT41 fusion protein.

TABLE 1

| 1 | 2 | 3 | 4 | 5 | 6 | 7 | 8 | 9 | 10 | 11 | pINT |
|---|---|---|---|---|---|---|---|---|----|----|------|
| Met ATG | Ala GCA | Thr ACA | Thr ACA | Ser TCA | Thr ACA | Ala GCA | Thr ACT | Thr ACG | — | Arg CGT | 41 |
| *** | *** | *** | **G | Thr A*T | Ser T*G | Thr A*G | **G | *** | — | *** | 42 |
| * | T | Ala G | * | Thr A*T | Ser T*T | Thr A*T | Ser T*A | * | — | * | 43 |
| *** | *** | *** | *** | *** | — | Asn AAC | Ser T*A | *** | — | *** | 60 |
| *** | *** | *** | *** | *** | *** | *** | *** | — | — | **A | 67d |
| *** | *** | *** | *** | *** | *** | *** | — | — | — | **A | 68d |
| *** | *** | *** | *** | *** | *** | — | — | — | — | **A | 69d, 72d |
| *** | *** | *** | *** | *** | *** | Gly *G* | Asn *A* | Ser T** | Ala GCA | **A | 90d, 91d |
| *** | *** | *** | *** | *** | *** | Lys AA* | — | — | — | **A | 93d |
| *** | *** | *** | *** | *** | *** | Pro C** | — | — | — | **A | 94d |
| *** | *** | *** | *** | *** | *** | Met ATG | — | — | — | **A | 95d |
| *** | *** | *** | *** | *** | *** | Gly *G* | — | — | — | **A | 96d |

EXAMPLE 2

Selection of additional clones

To detect additional suitable clones, a method according to Helfman, D.M. et al. (Proc. Natl. Acad. Sci. USA 80:31-35, 1983) is used. TP-agar dishes, the medium of which contains an additional 40 μm/ml IAA, are utilized for this purpose. Fifteen minutes before use, the agar surface of the plates is coated with a 2-mm thick TP top agar layer, a nitrocellulose filter is placed on the latter and freshly transformed cells are placed on the filter. Copies are made of the filters which have grown bacteria colonies following incubation at 37° C., and the bacteria from the original filter are lysed. To accomplish this, the filters are exposed to a chloroform atmosphere in an desiccator for 15 minutes, subsequently moved slowly for six hours at room temperature in immune buffer (50 mM tris of pH 7.5, 150 mM NaCl, 5 mM MgCl$_2$, and 3% (w/v) BSA), which contains an additional 1 μg/ml DNase I and 40 μg/ml lysozyme, and then washed twice for five minutes in washing buffer (50 mM tris of pH 7.5 and 150 mM NaCl). The filters are then incubated overnight at 3° C. in immune buffer with insulin-specific antibodies, washed four times for five minutes with washing buffer, incubated for one hour in immune buffer with a protein A-horseradish peroxidase conjugate, washed again four times for five minutes with washing buffer and colonies that have bound antibodies are visualized with a color reaction. Clones pINT42 and pINT43, which also produce fairly large quantities of fusion protein, are found in this manner in 500 colonies. The DNA obtained by sequencing and the amino acid sequence derived from it have also been reproduced in Table 1.

EXAMPLE 3

Preparation of plasmid pINT41d.

Between the relication origin and the trp-promoter, plasmid pINT41 contains a nonessential DNA region which is flanked by cleavage sites for enzyme Nsp(7524)1. To remove this region from the plasmid, pINT41 is cut with NSP(7524)1, and the larger of the resulting fragments is isolated and religated. This give rise to plasmid pINT41d, the DNA sequence of which is reproduced in Table 2.

TABLE 2

DNA-Sequence of Plasmid pINT41d

```
         10                    30                    50
GTGTCATGGTCGGTGATCGCCAGGGTGCCGACGCGCAGCTCGACTTGCACGGTGCACCAA 70                    90                    110
TGCTTCTGGCGTCAGGCAGCCATCGGAAGCTGTGGTRATGGCTGTGCAGGTCGTAAATCAC 130                   150                   170
TGCATAATTCGTGTCGCTCAAGGCGCACTCCCGTTCTGGATAATGTTTTTTGCGCCGACA 190                   210                   230
TCATAACGGTTCTGGCAAATATTCTGAAATGAGCTGTTGACAATTAATCATCGAACTAGT 250                   270                   290
TAACTAGTACGCAAGTTCACGTAAAAAGGGTATCGACCATGGCAACAACATCAACAGCAA 310                   330                   350
CTACGCGTTTCGTGAACCAGCACCTGTGCGGCTCCCACCTAGTGGAAGCTCTCTACCTGG 370                   390                   410
TGTGCGGGGAGCGAGGCTTCTTCTACACACCCAAGACCCGCCGGGAGGCAGAGGACCCTC 430                   450                   470
AGGTGGGGCAGGTGGAGCTGGGCGGGGGCCCTGGCGCAGGCAGCCTGCAGCCCTTGGCGC 490                   510                   530
TGGAGGGGTCCCTGCAGAAGCGCGGCATCGTGGAGCAGTGCTGCACCAGCATCTGCTCCC 550                   570                   590
TCTACCAGCTGGAGAACTACTGCAACTAATAGTCGACCTTTGCTTTCATTGTCGATGATA 610                   630                   650
AGCTGTCAAACATGAGAATTAGCCCGCCTAATGAGCGGGCTTTTTTTTAATTCTTGAAGA 670                   690                   710
CGAAAGGGCCTCGTGATACGCCTATTTTTATAGGTTAATGTCATGATAATAATGGTTTCT 730                   750                   770
TAGACGTCAGGTGGCACTTTTCGGGGAAATGTGCGCGGAACCCCTATTTGTTTATTTTTC 790                   810                   830
TAAATACATTCAAATATGTATCCGCTCATGAGACAATAACCCTGATAAATGCTTCAATAA 850                   870                   890
TATTGAAAAAGGAAGAGTATGAGTATTCAACATTTCCGTGTCGCCCTTATTCCCTTTTTT 910                   930                   950
GCGGCATTTTGCCTTCCTGTTTTTGCTCACCCAGAAACGCTGGTGAAAGTAAAAGATGCT 970                   990                   1010
GAAGATCAGTTGGGTGCACGAGTGGGTTACATCGAACTGGATCTCAACAGCGGTAAGATC 1030                  1050                  1070
CTTGAGAGTTTTCGCCCCGAAGAACGTTTTCCAATGATGAGCACTTTTAAAGTTCTGCTA 1090                  1110                  1130
TGTGGCGCGGTATTATCCCGTGTTGACGCCGGGCAAGAGCAACTCGGTCGCCGCATACAC 1150                  1170                  1190
TATTCTCAGAATGACTTGGTTGAGTACTCACCAGTCACAGAAAAGCATCTTACGGATGGC 1210                  1230                  1250
ATGACAGTAAGAGAATTATGCAGTGCTGCCATAACCATGAGTGATAACACTGCGGCCAAC 1270                  1290                  1310
TTACTTCTGACAACGATCGGAGGACCGAAGGAGCTAACCGCTTTTTTGCACAACATGGGG
```

TABLE 2-continued

DNA-Sequence of Plasmid pINT41d

```
        1330              1350              1370
GATCATGTAACTCGCCTTGATCGTTGGGAACCGGAGCTGAATGAAGCCATACCAAACGAC 1390              1420              1430
GAGCGTGACACCACGATGCCTGCAGCAATGGCAACAACGTTGCGCAAACTATTAACTGGC 1450              1470              1490
GAACTACTTACTCTAGCTTCCCGGCAACAATTAATAGACTGGATGGAGGCGGATAAAGTT 1510              1530              1550
GCAGGACCACTTCTGCGCTCGGCCCTTCCGGCTGGCTGGTTTATTGCTGATAAATCTGGA 1570              1590              1610
GCCGGTGAGCGTGGGTCTCGCGGTATCATTGCAGCACTGGGGCCAGATGGTAAGCCCTCC 1630              1650              1670
CGTATCGTAGTTATCTACACGACGGGGAGTCAGGCAACTATGGATGAACGAAATAGACAG 1690              1710              1730
ATCGCTGAGATAGGTGCCTCACTGATTAAGCATTGGTAACTGTCAGACCAAGTTTACTCA 1750              1770              1790
TATATACTTTAGATTGATTTAAAACTTCATTTTTAATTTAAAAGGATCTAGGTGAAGATC 1810              1830              1850
CTTTTTGATAATCTCATGACCAAAATCCCTTAACGTGAGTTTTCGTTCCACTGAGCGTCA 1870              1890              1910
GACCCCGTAGAAAAGATCAAAGGATCTTCTTGAGATCCTTTTTTTCTGCGCGTAATCTGC 1930              1950              1970
TGCTTGCAAACAAAAAAACCACCGCTACCAGCGGTGGTTTGTTTGCCGGATCAAGAGCTA 1990              2010              2030
CCAACTCTTTTTCCGAAGGTAACTGGCTTCAGCAGAGCGCAGATACCAAATACTGTCCTT 2050              2070              2090
CTAGTGTAGCCGTAGTTAGGCCACCACTTCAAGAACTCTGTAGCACCGCCTACATACCTC 2110              2130              2150
GCTCTGCTAATCCTGTTACCAGTGGCTGCTGCCAGTGGCGATAAGTCGTGTCTTACCGGG 2170              2190              2210
TTGGACTCAAGACGATAGTTACCGGTAAGGCGCAGCGGTCGGGCTGAACGGGGGGTTCGT 2230              2250              2270
GCACACAGCCCAGCTTGGAGCGAACGACCTACACCGAACTGAGATACCTACAGCGTGAGC 2290              2310              2330
ATTGAGAAAGCGCCACGCTTCCCGAAGGGAGAAAGGCGGACAGGTATCCGGTAAGCGGCA 2350              2370              2390
GGGTCGGAACCAGGAGAGCGCACGAGGGAGCTTCCAGGGGGAAACGCCTGGTATCTTTATA 2410              2430              2450
GTCCTGTCGGGTTTCGCCACCTCTGACTTGAGCGTCGATTTTTGTGATGCTCGTCAGGGG 2470              2490              2510
GGCGGAGCCTATGGAAAAACGCCAGCAACGCGGCCTTTTTACGGTTCCTGGCCTTTTGCT 2530              2550              2570
GGCCTTTTGCTCACATGTGTCAGAGGTTTTCACCGTCATCACCGAAACGCGCGAGGCAGC
TG
```

EXAMPLE 4

Fermentation and processing of pINT41d-fusion protein (i) Fermentation: A shaking culture in LB medium is prepared from *E. coli* W3110 transformed with pINT41d. Fifteen μl of this culture, which has an OD =2 are then put into 15.7 1 TP medium and the suspension is fermented 16 hours at 37° C. The culture, which at this time has an OD=13, is then adjusted to 20 μg/ml IAA, and until the end of fermentation, after another five hours, a 50% (w/v) maltose solution is continuously pumped in at a rate of 100 ml/hour. An OD=17.5 is attained in this process. At the end, the bacteria are harvested by centrifugation.

(ii) Rupture of Cells: The cells are resuspended in 400 ml/disintegration buffer (10 mM tris of pH 8.0, 5 mM EDTA) and disrupted in a French press. The fusion protein containing insulin is subsequently concentrated by 30 minutes of centrifugation at 23,500 g and washed with disintegration buffer. This yields 134 g sediment (moist substance).

(iii) Sulfitolysis: 12.5 g sediment (moist substance) from (ii) are stirred into 125 ml of an 8 M urea solution at 35° C. After stirring for thirty minutes, the solution is adjusted to pH 9.5 with sodium hydroxide solution and reacted with 1 g sodium sulfite. After an additional thirty minutes of stirring at 35° C., 0.25 g sodium tetrathionate is added and the mixture is again stirred for thirty minutes at 35° C.

(iv) DEAE-Anion exchange chromatography: The entire batch of (iii) is diluted with 250 ml buffer A (50 mM glycine, pH 9.0) and placed on a chromatography column which contains Fractogel® TSK DEAE-650 (column volume 130 ml, column diameter 26 mm) equilibrated with buffer A. After washing with buffer A, the fusion protein-S-sulfonate is eluted with a salt gradient consisting of 250 ml each buffer A and buffer B (50 mM glycine of pH 9.0, 3 M urea and 1 M NaCl) at a flow rate of 3 ml/minute. The fractions containing fusion protein-S-sulfonate are then combined.

(v) Folding and enzymatic cleavage: The combined fractions from (iv) are diluted at 4° C. in a volume ratio of 1+9 with folding buffer (50 mM glycine, pH 10.7) and per liter of the resulting dilution 410 mg ascorbic acid and 165 µl 2-mercaptoethanol are added at 4° C. under gentle stirring. After correction of the pH value to pH 10.5, stirring is continued for another 4 hours at 4° C. Subsequently, solid N-(2-hydroxyethyl)-piperazine-N'-2-ethane sulfonic acid (HEPES) is added to an end concentration of 24 g per batch-liter. The mixture which now has pH 8 is digested with trypsin at 25° C. During the process, the enzyme concentration in the digestion mixture is 80 µg/l. The cleavage course is followed analytically by RP-HPLC. After two hours, digestion can be stopped by addition of 130 µg soy bean trypsin inhibitor. HPLC shows the formation of 19.8 mg di-Arg insulin from a mixture according to (iii). The identity of the cleavage product is confirmed by protein sequencing and comparative HPLC with reference substances. The di-Arg insulin can be chromatographically purified according to known methods and transformed to insulin with carboxypeptidase B.

EXAMPLE 5

Construction of plasmid pINT60

Plasmid pINT60 results in an insulin precursor, the ballast sequence of which consists of only nine amino acids. For construction of this plasmid, plasmid pINT40 is cut with Nco and MluI and the resulting vector fragment is isolated. The oligonucleotide Insu15

TTCGGGTACCGTTGTTGTAGTTTGAGTTGCGCAG 5'
TTGCCCATGGC 3' is then synthesized, filled in with Klenow polymerase and also cut with these two enzymes. The resulting DNA fragment is then ligated with the vector fragment to yield plasmid pINT60.

Table 1 shows the DNA and amino acid sequence of the ballast constituent in this fusion protein.

EXAMPLE 6

Construction of plasmid pINT67d

Plasmid pINT67d is a derivative of pINT41d in which the codon of the amino acid in position nine of the ballast sequence is deleted. That is why, like pINT60, it results in an insulin precursor with a ballast sequence of nine amino acids. A method according to Ho, S. N. et al. (Gene 77:51-59, 1989) is used for its construction. For this purpose, two separate PCR's are first performed with plasmid pINT41d and the two oligonucleotide pairs TIR: 5'-CTG AAA TGA GCT GTT GAC-3'
and
DTR8: 5'-CAC AAA TCG AGT TGC TGT TGA TGT TGT-3'
or
DTR9: 5'-ACA GCA ACT CGA TTT GTG AAC CAG CAC-3'
and
Insu11: 5'-TCA TGT TTG ACA GCT TAT CAT-3'.

This produces two fragments that are partially complementary to each other and when annealed with each other code a similar insulin precursor as pINT41d in which, however, the amino acid in position nine is absent. For completion, the two fragments are combined and subjected to another PCR together with the oligonucleotides TIR and Insu11. From the DNA fragment obtained in this manner, the structural gene of the insulin precursor is liberated with Nco and SalI and purified. Plasmid pINT41d is then also cut with these two enzymes, the vector fragment is purified and subsequently ligated with the structural gene fragment from the PCR to yield plasmid pINT67d.

The nucleotide and amino acid sequences for the ballast region have been reproduced in Table 1.

EXAMPLE 7

Construction of plasmid pINT68d

Like plasmid pINT67d, plasmid pINT68d is a shortened derivative of plasmid pINT41d in which the codons of the two amino acids in positions eight and nine of the ballast sequence are deleted. It therefore results in an insulin precursor with a ballast sequence of only eight amino acids. The procedure previously described in Example 6 is used for its construction but with two oligonucleotide pairs TIR: 5'-CTG AAA TGA GCT GTT GAC-3'
and
DTR10: 5'-CAC AAA TCG TGC TGT TGA TGT TGT TGC-3'
or
DTR11: 5'-TCA ACA GCA CGA TTT GTG AAC CAG CAC-3'
and
Insu11: 5'-TCA TGT TTG ACA GCT TAT CAT-3'.

The nucleotide and amino acid sequences for the ballast region have been reproduced in Table 1.

EXAMPLE 8

Construction of plasmid pINT69d

Plasmid pINT69d is also a shortened derivative of plasmid pINT41d in which, however, the codons of the three amino acids in positions seven, eight and nine of the ballast sequence have been deleted. It therefore results in an insulin precursor with a ballast sequence of only seven amino acids. The procedure described in Example 6 is also used for its construction but with the two oligonucleotide pairs TIR: 5'-CTG AAA TGA GCT GTT GAC-3'
and
DTR12: 5'-CAC AAA TCG TGT TGA TGT TGT TGC CAT-3'
or
DTR13: 5'-ACA TCA ACA CGA TTT GTG AAC CAG CAC-3'
and
Insu11: 5'-TCA TGT TTG ACA GCT TAT CAT-3'

The nucleotide and amino acid sequences for the ballast region have been reproduced in Table 1.

EXAMPLE 9

Construction of plasmid pINT72d

Plasmid pINT72d is a derivative of plasmid pINT69d in which the entire C-peptide gene region, with the exception of the first codon for the amino acid arginine, is deleted. Consequently, this results in a "miniproinsulin derivative" with an arginine residue instead of a C-chain. With plasmid pINT69d as a starting point, the procedure described in Example 6 is also used for its construction but with the two oligonucleotide pairs

```
TIR:    5'-CTG AAA TGA GCT GTT GAC-3'
        and
Insu28: 5'-GAT GCC GCG GGT CTT GGG TGT-3'
        or
Insu27: 5'-AAG ACC CGC GGC ATC GTG GAG-3'
        and
Insu11: 5'-TCA TGT TTG ACA GCT TAT CAT-3'.
```

EXAMPLE 10

Construction of plasmids pINT73d, pINT88d and pINT89d

Plasmid pINT73d is a derivative of plasmid pINT69d (Example 8), in which the insulin precursor gene is arranged two times in succession. The plasmid therefore results in the formation of a polycistronic mRNA, which can double the yield. For its construction, a PCR reaction is carried out with plasmid pINT69d and the two oligonucleotides

```
Insu29: 5'-CTA GTA CTC GAG TTC AC-3'
        and
Insu11: 5'-TCA TGT TTG ACA GCT TAT CAT-3'.
```

This gives rise to a fragment with the insulin precursor gene and the pertinent ribosome binding site which in its 5'-end region has a cleavage site for enzyme XhoI and in its 3'-end region a cleavage site for SalI. The fragment is cut with the two above-mentioned enzymes and purified. Plasmid pINT69d is then linearized with SalI, the two DNA ends produced are dephosphorylated with phosphatase (from calf intestine) and ligated with the fragment from the PCR reaction to yield plasmid pINT73d.

In an analogous manner there are obtained plasmids pINT88d and pINT89d when plasmid pINT72d (Example 9) is modified analogously by arranging the "miniproinsulin gene" twice or thrice in sequence.

EXAMPLE 11

Construction of plasmid pINL41d

The starting plasmid pRUD3 has a structure analogous to that of plasmid pGATTP. However, instead of the trp-promoter region, it contains a tac-promoter region which is flanked by cleavage sites for enzymes EcoRI and Nco. The plasmid is cut with EcoRI, whereupon the protruding ends of the cleavage site are filled in with Klenow polymerase. Cutting is performed subsequently with Nco and the ensuing promoter fragment is isolated.

The trp-promoter of plasmid pINT41d is flanked by cleavage sites for enzymes PvuII and Nco. Since the plasmid has an additional cleavage site for PvuII, it is completely cut with Nco, but only partially with PvuII. The vector fragment, which is missing only the promoter region, is then isolated from the ensuing fragments. This is then ligated with the tac-promoter fragment to yield plasmid pINL41d

EXAMPLE 12

Construction of plasmid pL41c

Plasmid pPL-lambda (which can be obtained from Pharmacia) has a lambda-pL-promoter region. The latter is flanked by nucleotide sequences:

```
5'GATCTCTCACCTACCAAACAAT3'
and
5'AGCTAACTGACAGGAGAATCC3'.

Oligonucleotides
LPL3: 5' ATGAATTCGATCTCTCACCTACCAAACAAT 3'
      and
LPL4: 5' TTGCCATGGGGATTCTCCTGTCAGTTAGCT 3'
``` are prepared for additional flanking of the promoter region with cleavage sites for enzymes EcoRI and Nco. A PCR is carried out with these oligonucleotides and pPL-lambda and the resulting promoter fragment is cut with EcoRI and Nco and isolated. Plasmid pINL41d is then also cut with these two enzymes and the ensuing vector fragment, which has no promoter, is then ligated with the lambda-pL-promoter fragment to yield plasmid pL41c.

EXAMPLE 13

Construction of plasmid pL41d

The trp-transcription terminator located between the resistance gene and the fusion protein gene in plasmid pL41c is not effective in E. coli strains that are suitable for fermentation (e.g. E. coli N4830-1). For this reason, a polycistronic mRNA and with it a large quantity of resistance gene product are formed in fermentation. To prevent this side reaction, the trp-terminator sequence is replaced by an effective terminator sequence of the E. coli-rrnB-operon. Plasmid pANGMA has a structure similar to that of plasmid pINT41d, but it has an angiogenin gene instead of the fusion protein gene and an rrnB-terminator sequence (from commercial plasmid pKK223-3, which can be obtained from Pharmacia) instead of the trp-terminator sequence. The plasmid is cut with PvuI and SalI and the fragment containing the rrnB-terminator is isolated. Plasmid pL41c is then also cut with these two enzymes and the fragment containing the insulin gene is isolated. The two isolated fragments are then ligated to yield plasmid pL41d.

EXAMPLE 14

Construction of plasmid pINTLI

To prepare a plasmid for general use in the expression of fusion proteins, the proinsulin gene of plasmid pINT41d is replaced by a polylinker sequence. This gene is flanked by cleavage sites for enzymes MluI and SalI. The plasmid is therefore cut with the help of the two above-mentioned enzymes and the vector fragment is isolated. This is then ligated, to yield plasmid pINTLI, with the following two synthetic oligonucleotides

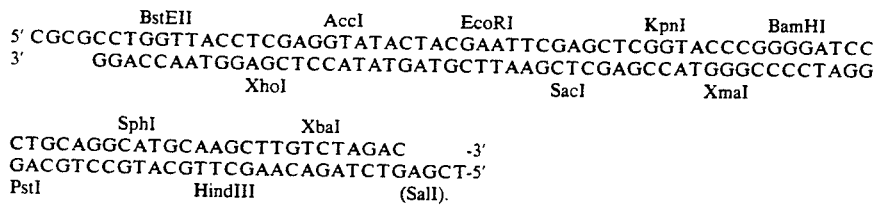

EXAMPLE 15

Insertion of a gene coding for HMG CoA-reductase (active domain) in pINTLI and expression of the fusion protein Table 3 represents the DNA and amino acid sequence of the gene HMG CoA-reductase. The synthetic gene for HMG CoA-reductase known from EP-A 0 292 803 (herein incorporated by reference) contains a cleavage site for BstEII in the region of amino acids Leu and Val in positions 3 and 4 (see Table 3). A protruding sequence corresponding to enzyme XbaI occurs at the end of the gene (in the noncoding area). The corresponding cleavage sites in the polylinker of plasmid pINTLI are in the same reading frame. Both cleavage sites are in each case singular.

Plasmid pUH10 contains the complete HMG gene (HMG fragments I, II, III, and IV), corresponding to the DNA sequence of table 3. Construction of pUH10 (FIG. 2) is described in EP-A 0 292 803 herein incorporated by reference. Briefly, special plasmids are prepared for the subcloning of the gene fragments HMG I to HMG IV and for the construction of the complete gene. These plasmids are derived from the commercially available vectors pUC18, pUC19 and M13mp18 or M13mp19, With the polylinker region having been replaced by a new synthetic polylinker corresponding to DNA sequence VI

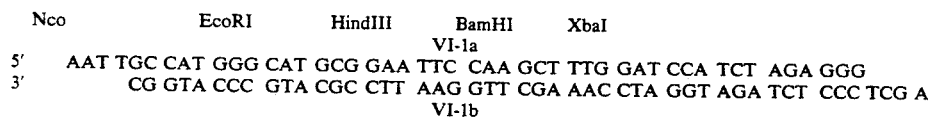

These new plasmids have the advantage that, in contrast to the pUC and M13mp plasmids, they allow the cloning of DNA fragments having the protruding sequences for the restriction enzyme Nco. Moreover, the recognition sequences for the cleavage sites Nco, EcoRI, HindIII, BamHI, and XbaI are contained in the vectors in exactly the sequence in which they are present in the complete gene HMG, which facilitates the sequential cloning and the construction of this gene. Thus it is possible to subclone the gene fragments HMG I to HMG IV in the novel plasmids. After the gene fragments have been amplified, it is possible for the latter to be combined to give the complete gene (see below).

a. Preparation of vectors which contain DNA sequence VI

DNA sequence VI may be prepared by standard techniques. The commercially available plasmid pUC18 (or pUC19, M13mp18 or M13mp19) is opened with the restriction enzymes EcoRI/HindIII as stated by the manufacturer. The digestion mixture is fractionated by electrophoresis on a 1% agarose gel. The plasmid bands which have been visualized by ethidium bromide staining are cut out and eluted from the agarose by electrophoresis. 20 fmol of the residual plasmid thus obtained are then ligated with 200 fmol of the DNA fragment corresponding to DNA sequence VI at room temperature overnight. A new cloning vector pSU18 (or pSU19, M13mUS18 or M13mUS19) is obtained. In contrast to the commercially available starting plasmids, the new plamids can be cut with the restriction enzyme Nco. The restriction enzymes EcoRI and HindIII likewise cut the plasmids only once because the polylinker which is inserted via the EcoRI and HindIII cleavage sites destroys those cleavage sites which are originally present.

b. Preparation of the hybrid plasmids which contain the gene fragments HMG I to HMG IV.

i) Plasmid containing the gene fragment HMG I

The plasmid pSU18 is cut open with the restriction enzymes EcoRI and Nco in analogy to the description in Example 15 (a) above, and is ligated with the gene fragment I which has previously been phosphorylated.

ii) Plasmid containing the gene fragment HMG II

The plasmids with the gene subfragments HMG II-1, II-2 and II-3 are subjected to restriction enzyme digestion with EcoRI/MluI, MluI/BssHII or BssHII/HindIII to isolate the gene fragments HMG II-1, HMG II-2 or HMG II-3, respectively. The latter are then ligated in a known manner into the plasmid pSU18 which has been opened with EcoRI/HindIII.

iii) Plasmid containing the gene fragment HMG III

The plasmids with the gene subfragments HMG III-1 and III-3 are digested with the restriction enzymes EcoRI/HindIII and then cut with Sau96I to isolate the gene fragment HMG III-1, or with BamHI/BanII to isolate the gene fragment HMG III-3. These fragments can be inserted with the HMG III-2 fragment into a pSU18 plasmid which has been opened with HindIII/BamHI.

iv) Plasmid containing the gene fragment HMG IV

Figure 2:
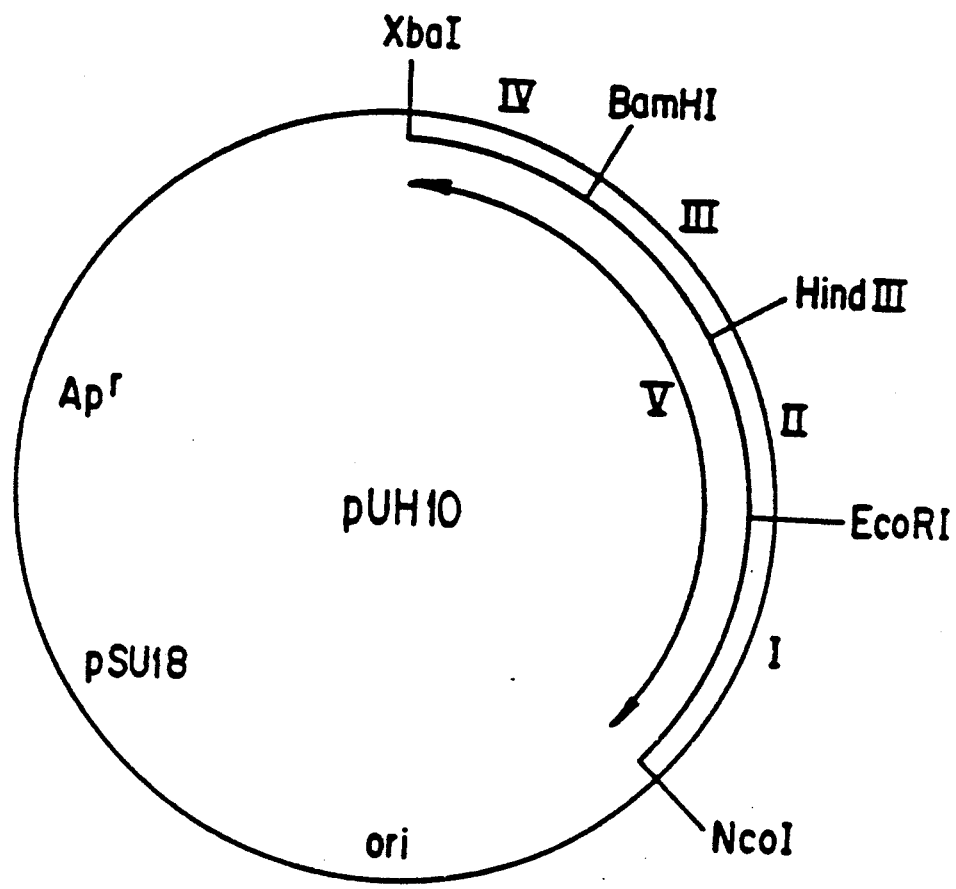
FIG. 2 is a map of plasmid pUH10 containing the complete HMG CoA reductase gene.

The plasmids with the gene subfragments HMG IV(1+2) and IV-(3+4) are opened with the restriction enzymes EcoRI/BamHI and EcoRI/XbaI, respectively, and the gene fragments HMG IV-(1+2) and HMG IV-(3+4) are purified by electrophoresis. The resulting fragments are then ligated into a pSU18 plasmid which has been opened with BamHI/XbaI and in which the EcoRI cleavage site has previously been destroyed with S1 nuclease as described below. A hybrid plasmid which still contains an additional AATT nucleotide sequence in the DNA sequence IV is obtained. The hybrid plasmid is opened at this point by digestion with the restriction enzyme EcoRI, and the protruding AATT ends are removed with S1 nuclease. For this purpose, 1 μg of plasmid is, after EcoRI digestion, incubated with 2 units of S1 nuclease in 50 mM sodium acetate buffer (pH 4.5), containing 200 mM NaCl and 1 mM zinc chloride, at 20° C. for 30 minutes. The plasmid is recircularized in a known manner via the blunt ends. A hybrid plasmid which contains the gene fragment IV is obtained.

c. Construction of the hybrid plasmid pUH10 which contains the DNA sequence V The hybrid plasmid with the gene fragment HMG I is opened with EcoRI/HindIII and ligated with the fragment HMG II which is obtained by restriction enzyme digestion of the corresponding hybrid plasmid with EcoRI/HindIII. The resulting plasmid is then opened with HindIII/BamHI and ligated with the fragment HMG III which can be obtained from the corresponding plasmid using HindIII/BamHI. The plasmid obtained in this way is in turn opened with BamHI/XbaI and linked to the fragment HMG IV which is obtained by digestion of the corresponding plasmid with BamHI/XbaI. The hybrid plasmid pUH10 which contains the complete HMG gene, corresponding to DNA sequence V, is obtained. FIG. 2 shows the map of pUH10 diagrammatically, with "ori" and "Ap<sup>r</sup>" indicating the orientation in the residual plasmid corresponding to pUC18.

If pINTLI is cut with BstEII and XbaI and the large fragment is isolated, and if, on the other hand, plasmid pUH10 (FIG. 2) is digested with the same enzymes and the fragment which encompasses most of the DNA sequence V from this plasmid is isolated, after ligation of the two fragments we obtain a plasmid which codes a fusion protein in which arginine follows the first eight amino acids in the ballast sequence of pINT41d (Table 1), which is followed, starting with Leu$^3$, by the structural gene of the active domain of HMG CoA-reductase. For purposes of comparison, the two initial plasmids are cut with enzymes Nco and XbaI and the corresponding fragments are ligated together, yielding a plasmid which codes, immediately after the start codon, the active domain of HMG CoA-reductase (in accordance with DNA sequence V of EP-A 0 292 803, see table 3).

Expression of the coded proteins occurs according to Example 4. Following the breakup of the cells, centrifugation is performed whereupon the expected protein of approximately 55 kDa is determined in the supernatant by gel electrophoresis. The band for the fusion protein is much more intensive here than for the protein expressed directly. Individual portions of 100 μl of the supernatant are tested in undiluted form, in a dilution of 1:10 and in a dilution of 1:100 for the formation of mevalonate. As an additional comparison, the fusion protein according to Example 4 (fusion protein with proinsulin constituent) is tested; no activity is apparent in any of the three concentrations. The fusion protein with the HMG CoA-reductase constituent exhibits maximum activity in all three dilutions, while the product of the direct expression shows graduated activity governed by the concentration. This indicates better expression of the fusion protein by a factor of at least 100.

TABLE 3

DNA sequence V + amino acid sequence I

```
        NcoI
        MET VAL LEU VAL THR GLN GLU PRO GLU ILE LEU GLU CYS LEU GLY ASN ALA GLU
     5' CATG GTT CTG GTT ACC CAG GAA CCT GAA ATT CTA CAG GAA TGT CTT GGT AAT GCA GAG
                                     10                          20
        PRO ARG GLU LEU PRO ASN GLU
        CCG CGG GAA CTT CCG AAT GAA

LYS GLY ALA LYS PHE LEU SER ASP ALA GLU ILE ILE GLN LEU VAL ASN ALA HIS   PRO ALA TYR LYS ILE GLU THR LEU MET GLU
        AAA GGT GCA AAG TTC CTT AGT GAT GCC GAG ATC ATC CAG CTT GTG AAT GCT CAT   CCA GCT TAC AAG CTC GAG ACT CTG ATG GAA
            30                              40                                       50

THR HIS GLU ARG GLY VAL SER ILE ARG ARG GLN LEU LEU SER LYS LYS LEU SER GLU LEU PRO SER   SER LEU GLN TYR LEU PRO TYR ARG ASP
        ACT CAT GAG CGT GGT GTA TCG ATT CGC CGA CAG CTT CTC TCG AAG AAA CTT TCT GAA CCG AGC TCT   CAG TAT CTG CCT TAT CGC GAT
            60                          70                              80

TYR ASN TYR SER LEU VAL MET GLY ALA CYS CYS GLU ASN VAL ILE GLY TYR MET PRO ILE   PRO VAL GLY PRO LEU CYS LEU
        TAT AAT TAC TCT TTG GTG ATG GGA GCC TGT TGT GAG AAT GTT ATT GGA TAT ATG CCC ATC   CCT GTG GGA GGA CCT CTT TGC TTG
            90                              100                             110

ASP GLU LYS GLU PHE GLN VAL PRO MET ALA THR ARG THR THR GLY CYS LEU VAL ALA SER   THR ASN ARG GLY CYS ARG ALA ILE GLY LEU GLY
        GAT GAA AAA GAA TTC CAG GTT CCA ATG GCA ACA AGA ACA GAA GGT TGT CTT GTG GCT TCT   ACC AAT AGA GGT TGC AGA GCG ATC GGT CTT GGT
            120                             130                             140

VAL LYS ASP GLU LYS GLY PHE GLN VAL PRO MET ALA THR ARG LEU PRO ARG ALA VAL   SER ALA CYS ASP SER ALA GLU VAL LYS
        (continuation sequence)
            150                             160                             170

ALA TRP LEU GLU THR SER GLU GLY PHE ALA VAL ILE LYS GLU ALA VAL CYS SER ALA VAL ILE PRO SER   ARG PHE ALA ARG LEU HIS THR
        GCA TGG CTC GAA ACA TCC GAA GGG TTC GCA GTG ATC AAG GAG GCA GTT TGT TCA GCA GTT ATT CCA AGC   AGG TTC GCG GCT CGC CTT CAT ACT
            180                             190                             200

SER ILE ALA GLY ARG ASN LEU TYR ILE ARG PHE GLN SER ARG SER ASP ALA MET GLY MET ASN MET ILE   SER LYS GLY THR GLU LYS
        AGT ATC GCT GGA CGC AAC CTT TAT ATC CGT TTC CAG AGA TCT GAC GCC ATG GGC ATG AAC ATG ATA TCT   AAG GGC ACA GAG AAA
            210                         220                         230

ALA LEU SER LYS LEU HIS GLU TYR PHE PRO GLU MET GLN ILE LEU ALA VAL SER TYR CYS THR ASP LYS   LYS PRO ALA ALA ILE
        GCA CTT TCC AAG CTT CAC GAG TAT TTT CCG GAG ATG CAG ATT CTG GCT GTT AGT TAT TGT ACT GAC AAG   AAA CCT GCT GCT ATC
            240                             250                             260

ASN TRP ILE GLU GLY MET GLY LYS SER VAL VAL CYS GLU ALA VAL ILE GLY SER TYR VAL VAL ARG GLU VAL   LEU LYS THR THR THR GLU
        AAT TGG ATT GAG GGT ATG GGA AAA TCT GTT GTT TGT GAA GCT GTA ATT CCA AGC GTT AGA GAA GTT TTA   AAG ACT ACC ACA GAG
            270                             280                             290

ALA MET ILE GLU VAL ASN LYS ASN LEU VAL GLY SER ALA MET ALA GLY TYR GLY TYR ASN ALA HIS   ALA ALA ASN ILE
        GCT ATG ATT GAG GTT AAT AAG AAT TTA GTG GGC TCT GCA ATG GCT GGA TAC AAC GCT CAT GCT AAC ATT
            300                             310                             320

VAL THR ALA ILE TYR ILE ALA CYS GLY GLN ASP ALA ALA GLN ASN VAL GLY SER SER ASN CYS ILE   THR LEU MET GLU ALA SER GLY PRO
        GTC ACC GCT ATC ATT TAT ATC GCT TGT GGC CAG GAC GCA GCA CAG AAT GTT GGA TCC TCT AAC TGT ATT   ACT TTA ATG GAA GCC TCA GGT CCG
            330                             340                             350

THR ASN GLU ASP LEU TYR ILE SER CYS THR MET PRO SER ILE GLU ILE GLY GLY THR VAL GLY GLY THR ASN LEU LEU PRO GLN GLN ALA
        ACA AAT GAA GAT TTA TAT ATC AGC TGC ACC ATG CCA TCT ATC GAG ATT GGT GGT ACC GTG GGT GGC ACC AAC CTT CTT CCA CAG CAG GCC
            360                             370                             380
```

TABLE 3-continued

DNA sequence V + amino acid sequence I

```
390                              400                              410
CYS LEU GLN MET LEU GLY VAL GLN GLY ALA CYS LYS ASP ASN ALA ARG GLN LEU ALA ARG ILE VAL CYS GLY THR VAL
TGT CTG CAA ATG TTG GGT GTT CAA GGA GCA TGC AAA GAT AAT GCC CGG CAA CTT GCA CGA ATT GTG TGT GGG ACC GTA 420                              430                              440
MET ALA GLY GLU LEU SER LEU MET ALA ALA LEU ALA ALA GLY HIS LEU VAL LYS SER HIS MET ILE HIS ASN ARG SER LYS ILE ASN LEU
ATG GCC GGC GAA TTG TCT CTT ATG GCT GCC TTG GCG GCC GGA CAT CTT GTC AAA TCT CAT ATG ATT CAC AAC CGT TCG AAG ATC AAT TTA 450                              460            XbaI
GLN ASP LEU GLN GLY ALA CYS THR LYS LYS THR ALA ... ...
CAG GAT CTG CAA GGC GCT TGC ACC AAG AAG ACA GCA TAA TAG T
```

EXAMPLE 16

Construction of plasmid pB70

Plasmid pINT41d is split with MluI and SalI and the large fragment is isolated. Plasmid pIK4 shown in FIG. 3a contains a gene for "mini-proinsulin," the C chain of which consists of arginine only.

The construction of this plasmid has previously been described in EP-A 0,347,781 (herein incorporated by reference). Briefly, the commercial plasmid pUC19 is opened using the restriction enzymes KpnI and PstI and the large fragment (FIG. 3-(1)) is separated through a 0.8% strength "Seaplaque" gel. This fragment is reacted with T4 DNA ligase using the DNA (FIG. 3-(2)) synthesized according to Table 4. Table 4 shows the sequence of gene fragment IK I, while table 5 represents the sequence of gene fragment IK II.

This ligation mixture then is incubated with competent E. coli 79/02 cells. The transformation mixture is plated out on IPTG/Xgal plates which contain 20 mg/l of ampicillin. The plasmid DNA is isolated from the white colonies and characterized by restriction and DNA sequence analysis. The desired plasmids are called pIK1 (FIG. 3).

Figure 3:
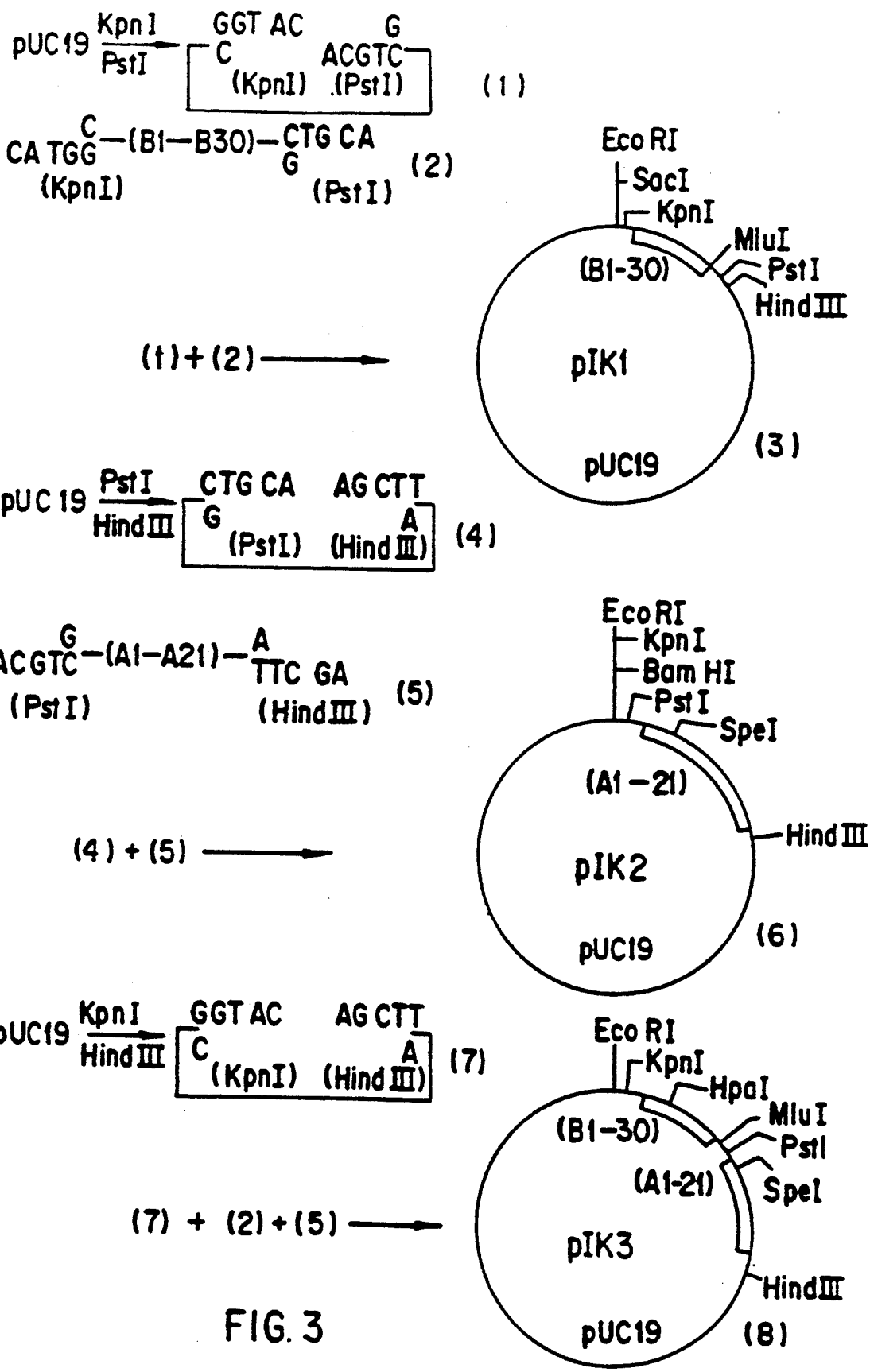
FIGS. 3 and 3a show construction of pIK4, a plasmid containing the mini-proinsulin gene.

Accordingly, the DNA (FIG. 3-(5)) according to Table 5 is ligated into pUC19 which has been opened using PstI and HindIII (FIG. 3-(4)). The plasmid pIK2 (FIG. 3) is obtained.

The DNA sequences (2) and (5) of FIG. 3 according to Table 4 and 5 are reisolated from the plasmids pIK1 and pIK2 and ligated with pUC19, which has been opened using KpnI and HindIII (FIG. 3-(7)). The plasmid pIK3 (FIG. 3) is thus obtained which encodes for a modified human insulin sequence.

Figure 3A:
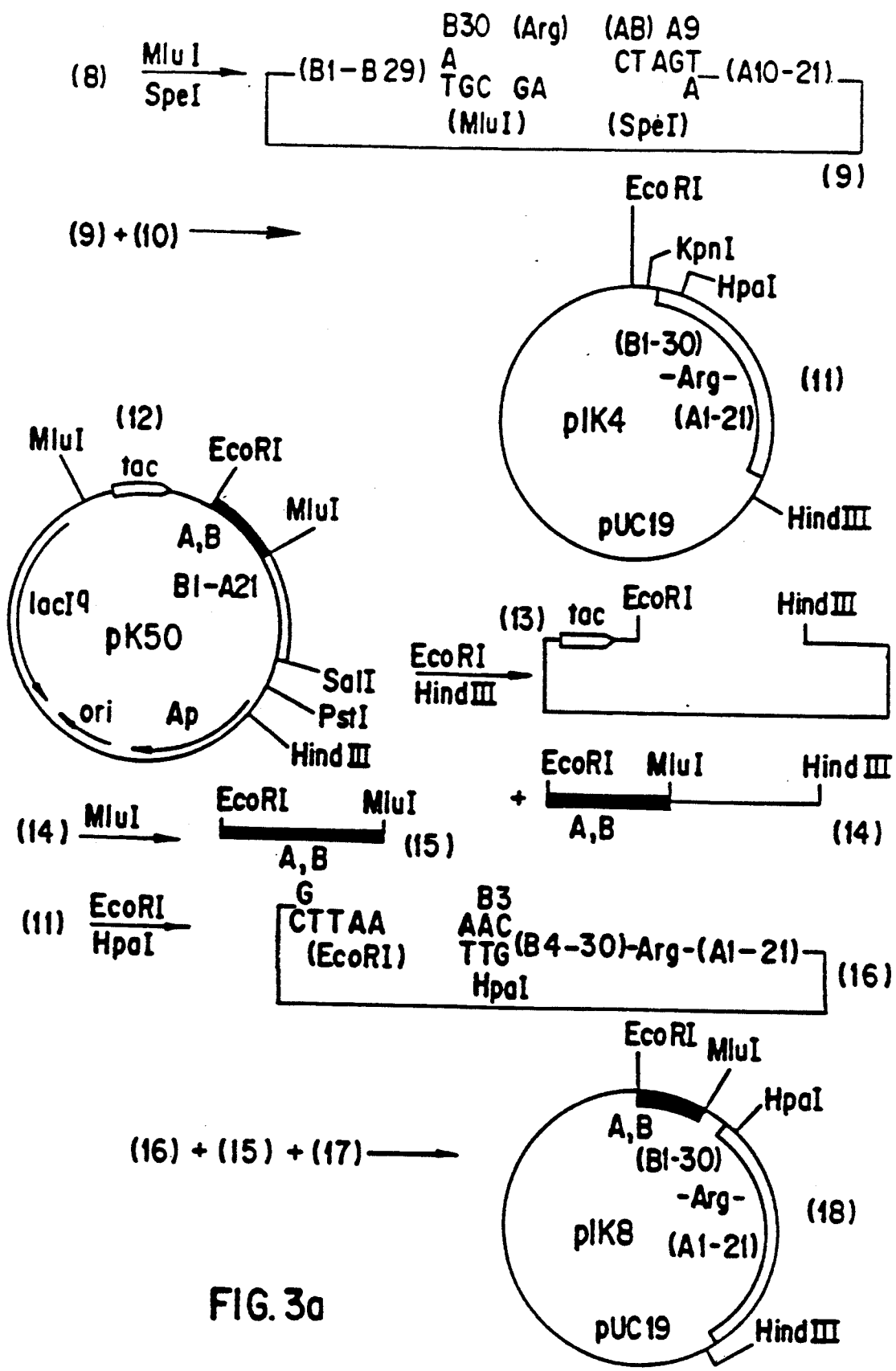

The plasmid pIK3 is opened using MluI and SpeI and the large fragment (FIG. 3a-(9)) is isolated. This is ligated with the DNA sequence (10).

```
       B30                A1  A2  A3  A4  A5  A6  A7  A8  A9
      (Thr) (Arg)         Gly Ile Val Glu Gln Cys Cys (Thr)(Ser)    (10)
   5'    CG  CGT          GGT ATC GTT GAA CAA TGT TGT A            3'
   3'         A           CCA TAG CAA CTT GTT ACA ACA TGA TC       5'
          (MluI)                                              (SpeI)
``` which supplements the last codon of the B chain (B30) by one arginine codon and replaces the excised codon for the first 7 amino acids of the A chain and supplements the codon for the amino acids 8 and 9 of chain. The plasmid pIK4 (FIG. 3a) is thus this obtained which encodes for human mini-proinsulin.

In tables 4 and 5, the B- and A-chains of the insulin molecule are in each case indicated by the first and last amino acid. Next to the coding region in gene fragment IK II, there is a cleavage site for SalI which will be utilized in the following construction.

Plasmid pIK4 is cut with HpaI and SalI and the gene coding "mini-proinsulin" is isolated. This gene is ligated with the above-mentioned large fragment of pINT41d and the following synthetic DNA sequence.

```
                          B1
      (Thr) Arg  Met  Gly  Arg  Phe
         CG CGT  ATG  GGC  CGT  TTC  GTT
            A    TAC  CCG  GCA  AAG  CAA
       (MluI)                         (HpaI)
```

This gives rise to plasmid pB70, which codes a fusion protein in which the ballast sequence (Table 1, line 1) is followed by amino acid sequence Met-Gly-Arg which is followed by the amino acid sequence of the "mini-proinsulin".

TABLE 4

Gene fragment IK I (2)

```
                    B1
                   Phe
         10         20             30              40
         <─────────────────────2────────────────────
         CT TTG GAC AAG AGA TTC GTT AAC CAA CAC TTG TGT GGT TCT CAC
     CAT GGA AAC CTG TTG TCT AAG CAA TTG GTT GTG AAC ACA CCA AGA GTG
         <─────────────1────────
      (KpnI)          HpaI
```

```
         50         60             70              80             90
         ─>  <─                                          ────4────
         TTG GTG GAA GCG TTG TAC TTG GTT TGT GGT GAG CGT GGT TTC TTC
         AAC CAC CTT CGC AAC ATG AAC CAA ACA CCA CTC GCA CCA AAG AAG
                                                  ─────3─────
```

```
              B30
             Thr Arg Lys Gly Ser Leu
        100       110         120
                                      ────────>
         TAC ACT CCA AAG ACG CGT AAG GGT TCT CTG CA
         ATG TGA GGT TTC TGC GCA TTC CCA AGA G
                                 ────>
                     MluI           (PstI)
```

TABLE 5

Gene fragment IK II (5)

```
              A¹
   Gln Lys Arg Gly
       130        140        150        160
   ←                                              ─ 6
        G AAG CGT GGT ATC GTT GAA CAA TGT TGT ACT AGT ATC TGT TCT
   AC GTC TTC GCA CCA TAG CAA CTT GTT ACA ACA TGA TCA TAG ACA AGA
   ←                                              ─ 5
   (PstI)                                    SpeI

A²¹
                     Asn
   170       180       190       200       210

─────────────────────────────────────────────→
   TTG TAC CAG CTG GAA AAC TAC TGT AAC TGA TAG TCG ACC CAT GGA
   AAC ATG GTC GAC CTT TTG ATG ACA TTG ACT ATC AGC TGG GTA CCT TCG A
   ─────────────────────────────────────────────→
                                              (HindIII)
```

EXAMPLE 17

By using the oligonucleotides listed below there are obtained plasmids pINT90d to pINT96d in analogy to the previous examples. An asterisk indicates the same encoded amino acid in the ballast constituent as in pINT42d.

pINT92 encodes a double mutation in the insulin derivative encoded by the plasmid pINT72d since the codon for Arg at the end of the ballast constituent and in the "mini C chain" is substituted by the codon for Met. Thus for expressed preproduct can be cleaved with cyanogen bromide.

```
pINT90d: ******GNSA* (variant of pINT69d)
TIR:      5'-CTGAAATGAGCTGTTGAC-3'
and
Insu50:   5'-TGCCGAATTTCCTGTTGATGTTGTTGC-3'
or
Insu49:   5'-GGAAATTCGGCACGATTTGTGAACCAG-3'
and
Insu11:   5'-TCATGTTTGACAGCTTATCAT-3' pINT91d: ******GNSA* (variant of pINT72d)
TIR:      5'-CTGAAATGAGCTGTTGAC-3'
and
Insu50:   5'-TGCCGAATTTCCTGTTGATGTTGTTGC-3'
or
Insu49:   5'-GGAAATTCGGCACGATTTGTGAACCAG-3'
and
Insu11:   5'-TCATGTTTGACAGCTTATCAT-3' pINT92d: (double mutant of pINT72d)
Insu56:   5'-TCGACCATGGCAACAACATCAACAATGTTTGTG-3
and
Insu58:   5'-GATGCCCATGGTCTT-3'
or
Insu57:   5'-AAGACCATGGGCATC-3'
and
Insu11:   5'-TCATGTTTGACAGCTTATCAT-3' pINT93d: ******(variant of pINT68d)
Insu53:   5'-ACCATGGCAACAACATCAACAAAACGATTTGTG-3'
and
Insu11:   5'-TCATGTTTGACAGCTTATCAT-3' pINT94d: ******(variant of pINT68d)
Insu54:   5'-ACCATGGCAACAACATCAACACCACGATTTGTG-3'
and
Insu11:   5'-TCATGTTTGACAGCTTATCAT-3' pINT95d: ******(variant of pINT68d)
Insu55:   5'-TCGACCATGGCAACAACATCAACAATGCGATTTGTG-3'
and
Insu11:   5'-TCATGTTTGACAGCTTATCAT-3' pINT96d: ******(variant of pINT68d)
Insu71:   5'-ACCATGGCAACAACATCAACAGGACGATTTGTG-3'
and
Insu11:   5'-TCATGTTTGACAGCTTATCAT-3'
```

We claim:

1. A process for the preparation of fusion proteins, which fusion proteins contain a desired protein and a ballast constituent, which process comprises
   (a) constructing a mixed oligonucleotide which codes for the said ballast constituent, wherein the said oligonucleotide contains the DNA sequence (coding strand)

$(DCD)_x$ in which D is A, G or T and x is 4 to 12,
   (b) inserting the said mixed oligonucleotide into a vector so that it is functionally linked to a regulatory region and to the structural gene coding for the said desired protein,
   (c) transforming host cells with the so-obtained vector population and
   (d) selecting from the transformants one or more clones expressing a fusion protein in high yield.

2. The process as claimed in claim 1, wherein the said oligonucleotide is designed so that it leads to a fusion protein which is soluble or which easily can be solubilized.

3. The process as claimed in claim 1, wherein x is 4 to 8.

4. The process as claimed in claim 1, wherein said oligonucleotide has the sequence (coding strand)

ATG GCW $(DCD)_{4-8}$ CGW in which W is A or T.

5. The process as claimed in claim 4, wherein the said oligonucleotide has the sequence

ATG GCA $(DCD)_{4-7}$ CGW.

6. The process as claimed in claim 1, wherein the said desired protein in a proinsulin and wherein the said oligonucleotide (coding strand) is ATG GCW $(DCD)_{y'}$ ACG CGW or ATG GCD $(DCD)_{y'}$ ACG CGT;

wherein D is A, G or T, W is A or T and y' is 3 to 6.

7. The process as claimed in claim 6, wherein y' is 4 to 6.

8. The process as claimed in claim 1, wherein the said oligonucleotide is designed so that the ballast constituent does not interfere with folding of the said desired protein.

9. The process as claimed in claim 8, wherein the said oligonucleotide has the sequence (coding strand)

ATG $(DCD)_y (NNN)_z$ wherein N stands for identical or different nucleotides, excluding stop codons for NNN, z is 1 to 4 and y+z is 6 to 12, y being at least 4.

10. The process as claimed in claim 9, wherein y+z is 6 to 10.

11. The process as claimed in claim 9, wherein y is 5 to 8 and z is 1.

12. The process as claimed in claim 1, wherein the said oligonucleotide codes at its 3' end of the coding strand for an amino acid or for a group of amino acids which allows an easy cleavage of the said desired protein from the said ballast constituent.

13. The process as claimed in claim 12, wherein said cleavage is an enzymatic cleavage.

14. The process as claimed in claim 12, wherein the desired protein is a proinsulin.

15. The process as claimed in claim 14, wherein the proinsulin has a C chain which is different from that of human proinsulin.

16. The process as claimed in claim 15, wherein the gene for C chain is designed so that the C chain can be split off together with the said ballast constituent.

17. The process as claimed in claim 16, wherein the C chain consists of arginine.

* * * * *

UNITED STATES PATENT AND TRADEMARK OFFICE
CERTIFICATE OF CORRECTION

PATENT NO. : 5,227,293

DATED : July 13, 1993

INVENTOR(S) : Stengelin et al.

It is certified that error appears in the above-indentified patent and that said Letters Patent is hereby corrected as shown below:

On the cover page, item [22] should read as follows:

"[22] PCT Filed: August 28, 1990 ".

On the cover page, under item [22] and before the section entitled "Related U.S. Application Data", the following should appear:

"[86]  PCT No.:    PCT/US90/04840
       § 371 Date:    April 23, 1992
       § 102(e) Date: April 23, 1992"

[87] PCT Pub. No.: WO91/03550
     PCT Pub. Date: March 21, 1991

In column 1, line 5, the word "co-pending" should be deleted.

In column 1, line 7, the word "abandoned" should read "(now abandoned)".

In column 2, line 62, the phrase "the fusion protein is" should read "a fusion protein which is".

In column 2, line 63, the comma appearing after the word "insoluable" should be deleted.

In column 5, line 41, the word "Nucleic" should be italicized.

In column 8, line 48, "$\mu$m/ml" should read "$\mu$g/ml".

In column 10, line 4, the word "relication" should read "replication".

In column 12, line 63, "ml/disintegration" should read "ml disintegration".

UNITED STATES PATENT AND TRADEMARK OFFICE
CERTIFICATE OF CORRECTION

PATENT NO. : 5,227,293
DATED : July 13, 1993
INVENTOR(S) : Stengelin et al.

It is certified that error appears in the above-indentified patent and that said Letters Patent is hereby corrected as shown below:

In column 18, line 61, "IV(1+2)" should read "IV-(1+2)".

In column 27, line 66, "pINT42d" should read "pINT41d".

In column 28, line 22, the word "for" which follows the word "Thus" should be deleted.

In column 29, second line of claim 6, the word "in" which follows the word "protein" should read "is".

In column 30, lines 1 and 3, the subscript "y," should read "y'".

Signed and Sealed this

Twenty-third Day of May, 1995

BRUCE LEHMAN

Attest:

Attesting Officer

Commissioner of Patents and Trademarks